(12) United States Patent
Nelson

(10) Patent No.: US 7,401,413 B1
(45) Date of Patent: Jul. 22, 2008

(54) DISPOSABLE WOUND MEASURING DEVICE

(76) Inventor: Chris L Nelson, 9797 Sidehill Rd., North East, PA (US) 16428

(*) Notice: Subject to any disclaimer, the term of this patent is extended or adjusted under 35 U.S.C. 154(b) by 43 days.

(21) Appl. No.: 11/676,782

(22) Filed: Feb. 20, 2007

(51) Int. Cl.
*A61B 5/103* (2006.01)
*A61F 13/00* (2006.01)

(52) U.S. Cl. .............................. 33/512; 33/562; 33/493; 33/836; 602/43; 128/897

(58) Field of Classification Search ................... 33/512, 33/511, 514.2, 562, 563, 566, 520, 836, 483–485, 33/491–494; 128/849, 850, 888, 897; 602/41–43, 602/52, 58
See application file for complete search history.

(56) References Cited

U.S. PATENT DOCUMENTS

| | | | |
|---|---|---|---|
| 1,587,133 A * | 6/1926 | Anhof | 283/115 |
| 2,529,058 A * | 11/1950 | Tell et al. | 33/555.4 |
| 2,579,664 A * | 12/1951 | Gleasman | 33/492 |
| 4,131,998 A | 1/1979 | Spears | |
| 4,389,782 A | 6/1983 | Webster | |
| 4,483,075 A | 11/1984 | Kundin | |
| 5,000,172 A | 3/1991 | Ward | |
| 5,197,465 A | 3/1993 | Montgomery | |
| 5,265,605 A | 11/1993 | Afflerbach | |
| D348,618 S * | 7/1994 | Leslie et al. | D10/64 |
| 5,379,754 A * | 1/1995 | Tovey et al. | 600/109 |
| 5,423,737 A | 6/1995 | Cartmell et al. | |
| 5,577,328 A * | 11/1996 | Kerry, Sr. | 33/563 |
| 5,605,165 A | 2/1997 | Sessions et al. | |
| 5,749,842 A * | 5/1998 | Cheong et al. | 602/41 |
| 5,807,280 A | 9/1998 | Davis | |
| D401,326 S | 11/1998 | Powell et al. | |
| 5,897,516 A | 4/1999 | Kadash et al. | |
| 6,159,167 A | 12/2000 | Hardin-Naser | |
| 6,622,728 B2 | 9/2003 | Rusin | |
| 6,706,940 B2 * | 3/2004 | Worthley | 602/57 |
| 2004/0015115 A1 * | 1/2004 | Sinyagin | 602/42 |
| 2004/0243073 A1 | 12/2004 | Lockwood et al. | |
| 2006/0258961 A1 * | 11/2006 | Zamierowski et al. | 600/587 |
| 2007/0107243 A1 * | 5/2007 | Newell | 33/511 |

FOREIGN PATENT DOCUMENTS

AU 9660726 A * 1/1997
CN 200994778 Y * 12/2007

* cited by examiner

*Primary Examiner*—G. Bradley Bennett
*Assistant Examiner*—Amy Cohen Johnson
(74) *Attorney, Agent, or Firm*—Wayne L. Lovercheck

(57) ABSTRACT

A disposable wound measuring device for making simultaneous three-dimensional (length, width and depth) measurements of a wound or ulcer to facilitate wound care assessment and healing that includes a flexible, clear plastic planar card or member superposed on the wound and having a centrally located aperture and concentric circles radially arranged about the aperture, and an elongated depth gauge insertable through the aperture and incrementally adjustable either vertically or obliquely through the aperture and relative to the wound surface and the plastic member for making a wound depth measurement with the depth gauge being retained in position by a plurality of beads equidistantly spaced along the gauge and slightly larger in diameter than the aperture thereby self-retaining the depth gauge in a particular position for making the wound depth measurement.

20 Claims, 8 Drawing Sheets

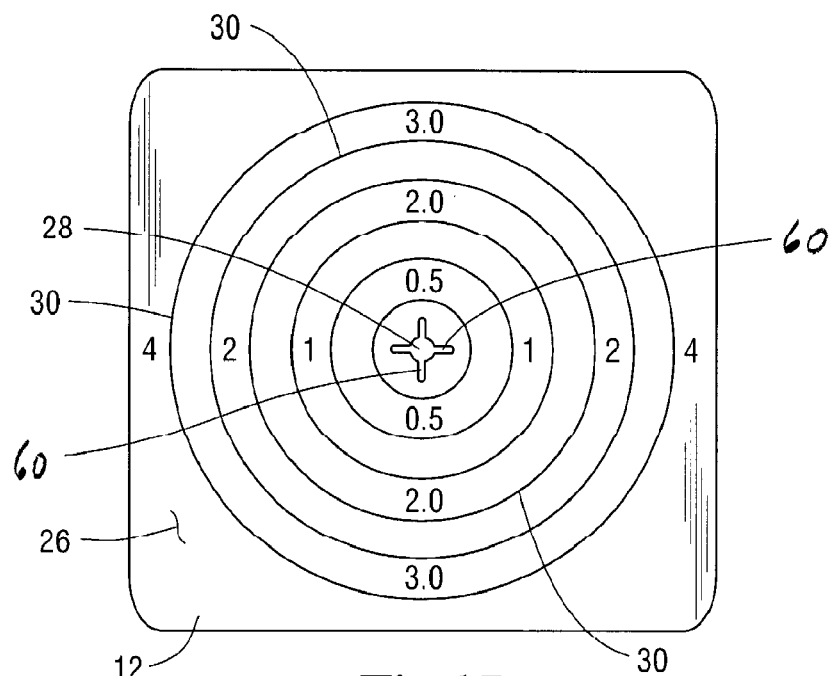
Fig.17
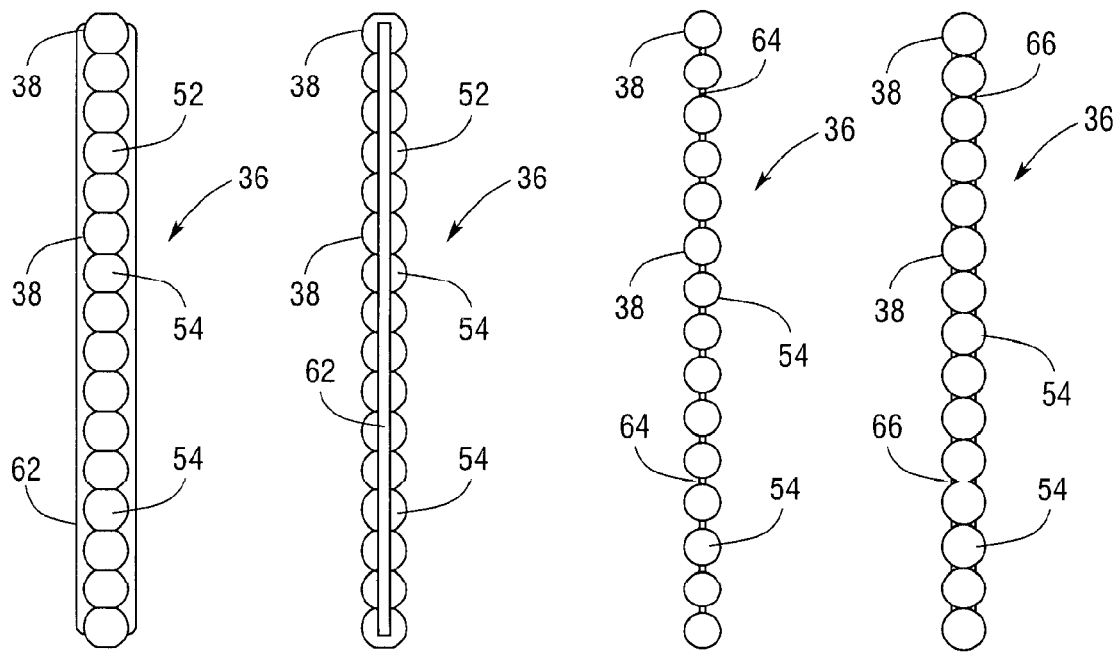
Fig.18A    Fig.18B    Fig.19    Fig.20

DISPOSABLE WOUND MEASURING DEVICE

FIELD OF THE INVENTION

The present invention pertains to methods and devices for wound assessment and care, and more particularly pertains to a disposable wound measuring device for simultaneously measuring the surface area and depth of a wound in order to facilitate wound care and treatment.

BACKGROUND OF THE INVENTION

The primary and foremost step in wound care is the assessment and documentation of the wound to ascertain its characteristics and features so that a medically informed decision can be made regarding the treatment of the wound. Wounds vary greatly in size, type and location. Some wounds are superficial and occur only in the first few layers of the skin. On the other hand, puncture wounds involve the perforation or penetration of an object through several tissue layers. Moreover wounds classified as ulcers are missing tissue substance, are usually cavernous or concave in shape, and can be found on all areas of the body. The etiology of a particular ulcer can vary greatly, and thus such wounds have a different nomenclature that is related to their specific diagnosis. For example, decubitis ulcers (commonly known as bedsores) are generally found on the sacrum, while neurotrophic ulcers have a predisposition for forming on the feet of diabetics. As the cause of a wound or ulcer is determined, a treatment regimen and wound care of the various ulcers will differ accordingly.

Thus, in treating wounds and ulcers, a paramount aspect of their care, both for determining healing and the effectiveness of wound management products, is an objective assessment of the characteristics and features of each wound. This assessment includes the evaluation of such characteristics and features that include the color, odor, temperature, and condition of the tissue (macerated, dry or presence of exudates). In addition, assessment must be made of the wound dimension that includes measurement of the size, depth, and shape of the wound. Moreover, features and characteristics such as wound location, presence of eschar, erythema, drainage, and undermining of site must also be assessed and evaluated. Thus, a timely and accurately recorded assessment provides the treating medical practitioner with a history and progress report of the wound features and wound healing; and such recorded assessment directly guides the chosen treatment regimen.

The prior art discloses a wide range of methods and devices for wound measurement and assessment. For example, methods and devices that measure surface area and depth include the Lockwood patent application publication (U.S. patent 2004/0243073 A1) and the Kundin patent (U.S. Pat. No. 4,483,075).

Devices and methods for measuring or outlining a wound, ulcer, blemish or tumor include the Spears patent (U.S. Pat. No. 4,131,998), the Webster patent (U.S. Pat. No. 4,389,782), the Ward patent (U.S. Pat. No. 5,000,172), the Afflerbach patent (U.S. Pat. No. 5,265,605), the Cartmell et al. patent (U.S. Pat. No. 5,423,737), the Sessions et al. patent (U.S. Pat. No. 5,605,165), the Kadash et al. patent (U.S. Pat. No. 5,897,516), and the Rusin patent (U.S. Pat. No. 6,622,728).

Devices and methods that incorporate an elongated member having depth measuring indicia thereon include the Powell et al. patent (U.S. Design Pat. No. 401,326), the Montgomery patent (U.S. Pat. No. 5,197,465), the Davis patent (U.S. Pat. No. 5,807,280), and the Hardin-Naser patent (U.S. Pat. No. 6,159,167).

General devices and methods for wound evaluation and measurement include the Wendelken et al. patent (U.S. Pat. No. 6,193,658 B1), the Herskovitz patent (U.S. Pat. No. 6,341,429 B1) and the Eichbaum patent (U.S. Design Pat. No. 318,244).

SUMMARY OF THE INVENTION

The present invention pertains to a disposable wound measuring device that provides for simple, immediate, reproducible and economical clinical wound care assessment. The disposable wound measuring device of the present invention allows the medical practitioner, specialist or professional to accurately track the healing process of the wound or ulcer while facilitating the gathering of all essential measurement data in order to provide a clear, accurate and compliant medical record of the history of the wound or ulcer from initial occurrence to complete healing and recovery.

The disposable wound measuring device of the present invention includes a flexible planar circular, square or rectangular shaped clear plastic member or card that is superposed upon the wound or ulcer. That plastic member needs to be flexible in order to conform to the shape and contour of the tissue, especially about the perimeter of the wound or ulcer. The flexibility of the plastic member allows the plastic member to establish the effective plane of the tissue that would exist in the absence of the wound or ulcer. The plastic member includes a centrally located aperture, and radially arranged about the aperture are a series of concentric circles extending adjacent to the perimeter of the plastic member. The radial spacing of the circles from each other is preferably at one half-millimeter increments or at one-millimeter increments.

In addition, the disposable wound measuring device includes a vertically oriented, elongated depth gauge or member that is inserted into and through the centrally located aperture for slidable adjustment through the aperture for determining wound depth. The elongated depth gauge includes a plurality of retaining beads spaced along the entire length of the depth gauge with the beads being spaced at graduated increments of either one half-millimeter or one millimeter. Each bead has a diameter that is slightly greater than the diameter of the centrally located aperture, and this allows for the depth gauge to be retained in position after the controlled and incremental advancement of the depth gauge to the base of the wound for contact thereagainst so that an accurate depth measurement can be made. Each bead thus provides for the incremental advancement of the depth gauge into the wound and then the self-retention in that respective position at the specific depth so that the measurement can be taken. The depth gauge is thus continuously slidable through the aperture for advancing into the wound or ulcer to make a depth measurement and then retained in that position by the inter-engagement of the beads with the aperture so that the entire device can be withdrawn from the wound and the depth measurement read. In addition to the depth gauge being slidably vertically adjustable through the aperture, the depth gauge is slidably adjustable through the aperture at angles that are oblique to the surface of the wound and the plastic member. This allows the device to determine the depth of a wound or ulcer wherein the greatest depth is determined to be at an angle that is oblique to the surface of the wound and to the plastic member.

It is an object of the present invention to provide a disposable wound measuring device for simultaneously measuring the length, width and depth of a wound or ulcer.

It is another object of the present invention to provide a disposable wound measuring device that simultaneously measures in three dimensions wound or ulcer characteristics and features.

It is yet another object of the present invention to provide a disposable wound measuring device that is flexible for conforming to the shape and contour of the tissue about the perimeter of the wound or ulcer site.

It is still yet another object of the present invention to provide a disposable wound measuring device that includes an elongated gauge graduated in one half-millimeter increments for accurately measuring the depth of the wound or ulcer.

It is still yet a further object of the present invention to provide a disposable wound measuring device that is disposable after use to prevent and avoid contamination.

Another object of the present invention is to provide a disposable wound measuring device whose dimensions can be varied to accommodate specific applications and for use on various anatomic sites.

Yet another object of the present invention is to provide a disposable wound measuring device that allows for a simple, immediate, reproducible and simultaneous three-dimensional clinical assessment of the wound for accurately tracking the healing process and gathering essential measurement data for creating a clear, accurate, and compliant medical record.

Yet still another object of the present invention is to provide a disposable wound measuring device that includes a flexible planar member having concentric circles and associated indicia printed thereon for measuring the surface area dimensions of the wound and the vertically oriented gauge for measuring the depth of the wound.

Yet still a further object of the present invention is to provide a disposable wound measuring device wherein the flexible planar member and the vertically oriented gauge function in conjunction with one another for providing simultaneous three-dimensional wound measurement and assessment.

Still another object of the present invention is to provide a disposable wound measuring device wherein the thickness of the flexible planar member is variable so that thicker planar members would be used for larger wounds and ulcers and thinner planar members would be used for smaller wounds and ulcers, especially those found in bodily or anatomic regions of more complex contours.

Still yet another object of the present invention is to provide a disposable wound measuring device wherein the gauge is axially and vertically slidably adjustable within and through the center of the planar member and can be maintained in any incrementally adjusted position for accurately measuring the depth of the wound or ulcer.

Still yet a further object of the present invention is to provide a disposable wound measuring device wherein the vertically oriented depth gauge is tapered distally for increasing depth measurement accuracy.

Another object of the present invention is to provide a disposable wound measuring device that is able to accurately measure the depth of a wound where the greatest depth is at an angle that is oblique to the surface of the wound and the disposition of the flexible planar member.

Another further object of the present invention is to provide a disposable wound measuring device wherein the numerical indicia associated with each concentric circle can be arranged at various radial positions relative to each circle for decreasing the need to reorient the planar member at the wound perimeter so that wounds ranging from small to large size can be better evaluated.

A further object of the present invention is to provide a disposable wound measuring device wherein each concentric circle can be alternately shaded and/or colored to radially differentiate that circle from adjoining circles for minimizing and lessening the incidence of error.

A still further object of the present invention is to provide a disposable wound measuring device wherein the scale of measurement with regard to the spacing of the circles on the planar member and the location of the measurement indicia on the depth gauge can be varied in proportion to wound size, type and anatomic site and location.

These and other objects, features and advantages will become apparent to those skilled in the art upon a perusal of the following detailed description read in conjunction with the accompanying drawing figures and appended claims.

BRIEF DESCRIPTION OF THE DRAWINGS

FIG. 17 is a top plan view of the disposable wound measuring device of the present invention illustrating the concentric measurement circles and the centrally-located aperture in cruciate or cross-shaped form and through which the ribs of the depth gauge slide;

FIG. 18a is a front elevational view of the disposable wound measuring device of the present invention illustrating the rib that join the beads of the depth gauge;

FIG. 18b is a side elevational view of the disposable wound measuring device of the present invention illustrating the longitudinal extension of the rib for adjoining the beads of the depth gauge;

FIG. 19 is a front elevational view of the disposable wound measuring device of the present invention illustrating an alternative embodiment for adjoining the beads in the form of a tubular member that connects the beads to each other in a coaxial and longitudinal arrangement; and FIG. 20 is a front elevational view of the disposable wound measuring device of the present invention illustrating another alternative embodiment for adjoining the beads in the form of a connecting member that connects the beads together and fills in the space between adjacent beads.

DETAILED DESCRIPTION OF THE PREFERRED EMBODIMENT

Illustrated in FIGS. 1 through 20 is a disposable wound or ulcer measuring device 10 for simultaneously measuring specific wound or ulcer parameter or features, and particularly the surface area and depth of a wound or ulcer. Thus, the contiguous placement of wound measuring device 10 of the present invention upon the wound or ulcer allows for the simultaneous measurement of the wound in the X-, Y- and Z-axes, i.e., the length, width and depth of the ulcer or wound. Wound measuring device 10 provides for simple, immediate, disposable, uncontaminated, economical, reproducible and three dimensional wound or ulcer care measurement and assessment so that all relevant measurement data can be collected for accurately tracking the healing process which results in a clear, accurate and compliant medical record of the ulcer or wound.

Figure 4:
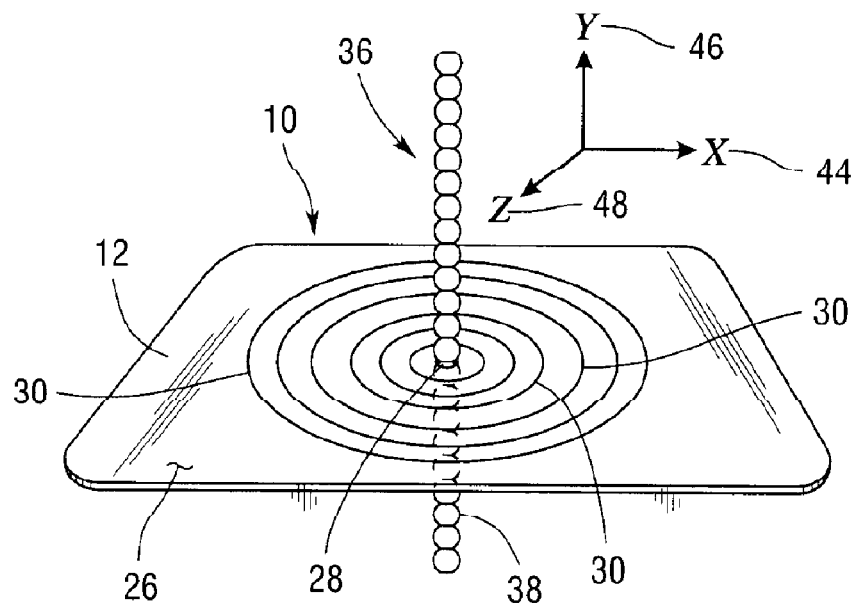
FIG. 4 is a perspective view of the disposable wound measuring device of the present invention illustrating the insertion of the depth gauge through the centrally located aperture of the clear plastic member and the simultaneous three-dimensional wound measurement capability along the x, y, and z axii.
Figure 5:
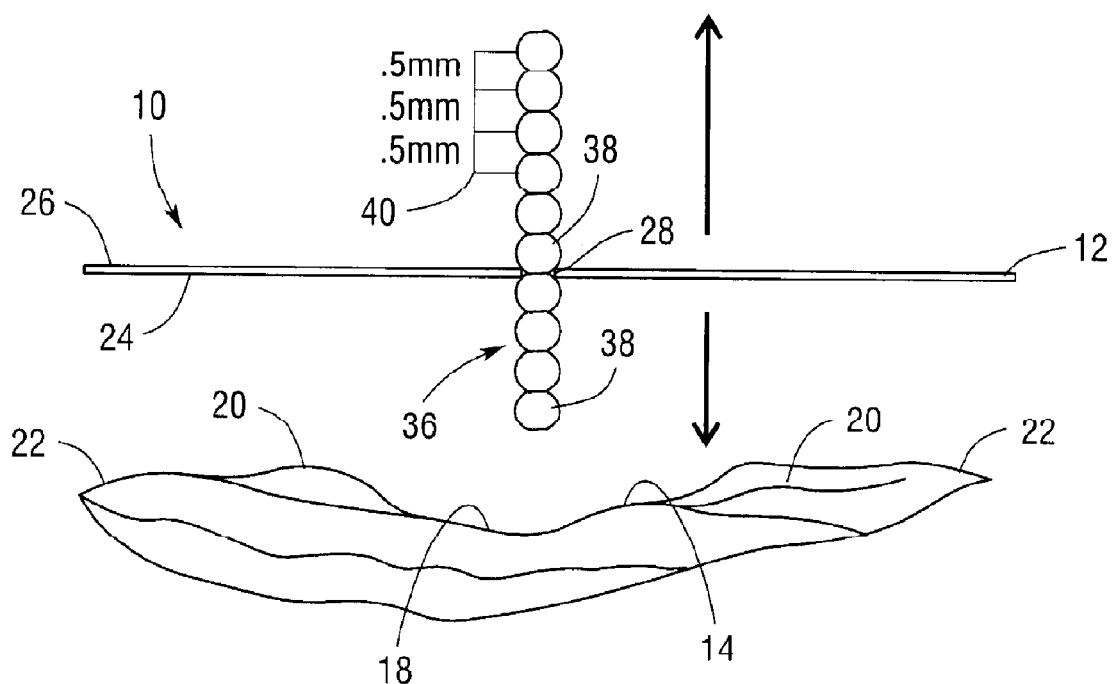
FIG. 5 is a side elevational view of the disposable wound measuring device of the present invention illustrating the vertical slidable reciprocable movement of the depth gauge relative to the clear plastic member for accurately and precisely measuring the depth of the wound.
Figure 6:
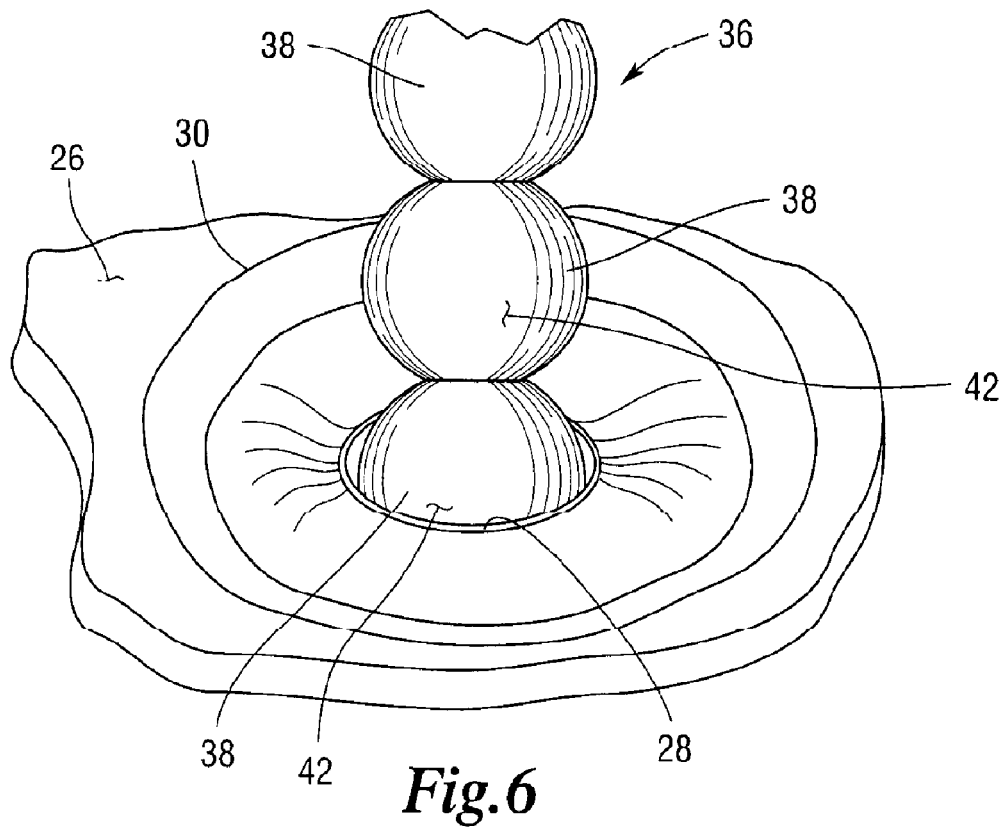
FIG. 6 is an enlarged perspective view of the disposable wound measuring device of the present invention illustrating the engagement of one retaining bead of the depth gauge with the centrally located aperture of the clear plastic member.
Figure 7:
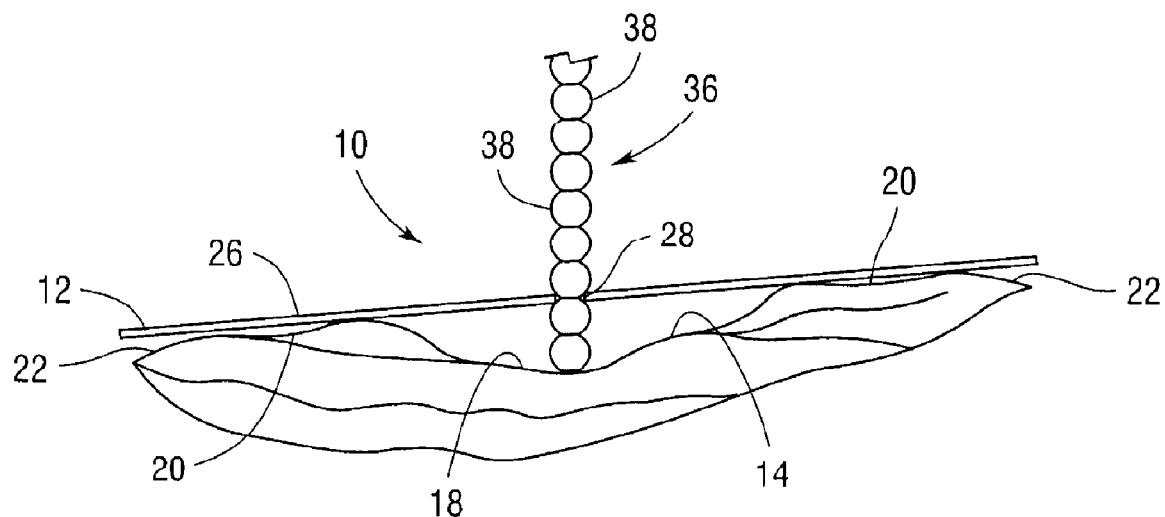
FIG. 7 is a side elevational view of the disposable wound measuring device of the present invention illustrating the insertion of the depth gauge down into the wound to measure the depth of the wound and the disposition of the clear plastic member upon the wound so that the simultaneous three dimensional measurement of the wound can occur.
Figure 8:
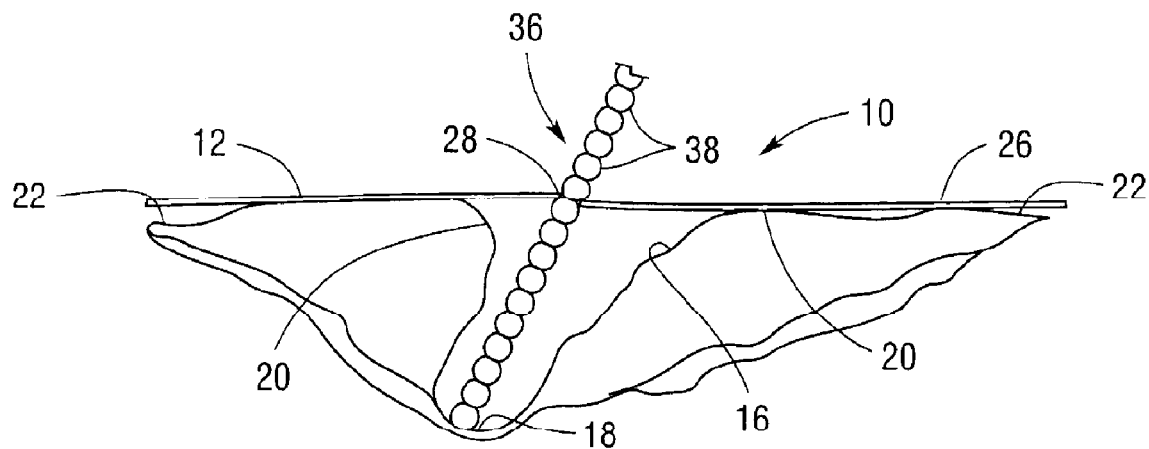
FIG. 8 is side elevational view of the disposable wound measuring device of the present invention illustrating the angled disposition of the depth gauge relative to the planar surface of the clear plastic card for measuring the depth of an oblique wound.

Thus, as shown in FIGS. 1 through 8 and 13 through 15, disposable wound measuring device 10 includes a generally rectangular-shaped clear plastic card or member 12 that is superimposed on the wound; such as standard wound 14 shown in FIGS. 5 and 7 or oblique wound 16 shown in FIG. 8. Each wound 14 or 16 has a deepest point, depth or base 18 that is measured in the Y-axis. In addition, each wound 14 and 16 has a margin or perimeter 20 that defines the extent of wound 14 or 16 on surface tissue 22. Plastic card or member 12 must be transparent for the proper alignment and orientation of plastic member 12 upon the site of wound 14 or 16. In addition, plastic member 12 is flexible so that plastic member 12 is able to conform to the shape and contour of tissue 22 adjacent and about perimeter 20 of wound 14 or 16, and to enable plastic member 12 to be placed contiguously on wound 14 or 16. When placed upon wound 14 or 16, as shown most distinctly in FIGS. 5, 7 and 8, clear plastic member 12 establishes the effective plane of the tissue that would exist in the absence of wound 14 or 16.

Figure 11:
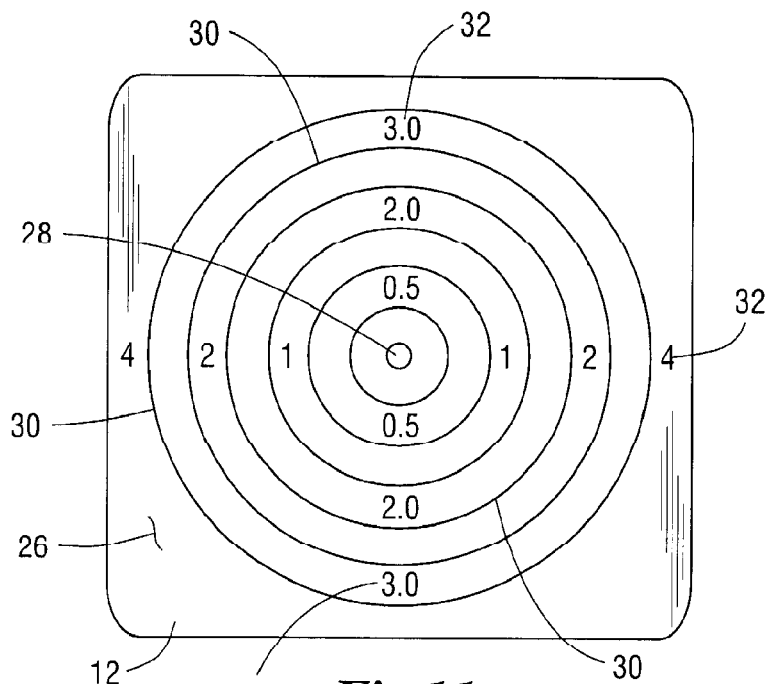
FIG. 11 is a top plan view of the disposable wound measuring device of the present invention illustrating an alternative embodiment for a clear plastic member that is used to measure smaller wounds.
Figure 13:
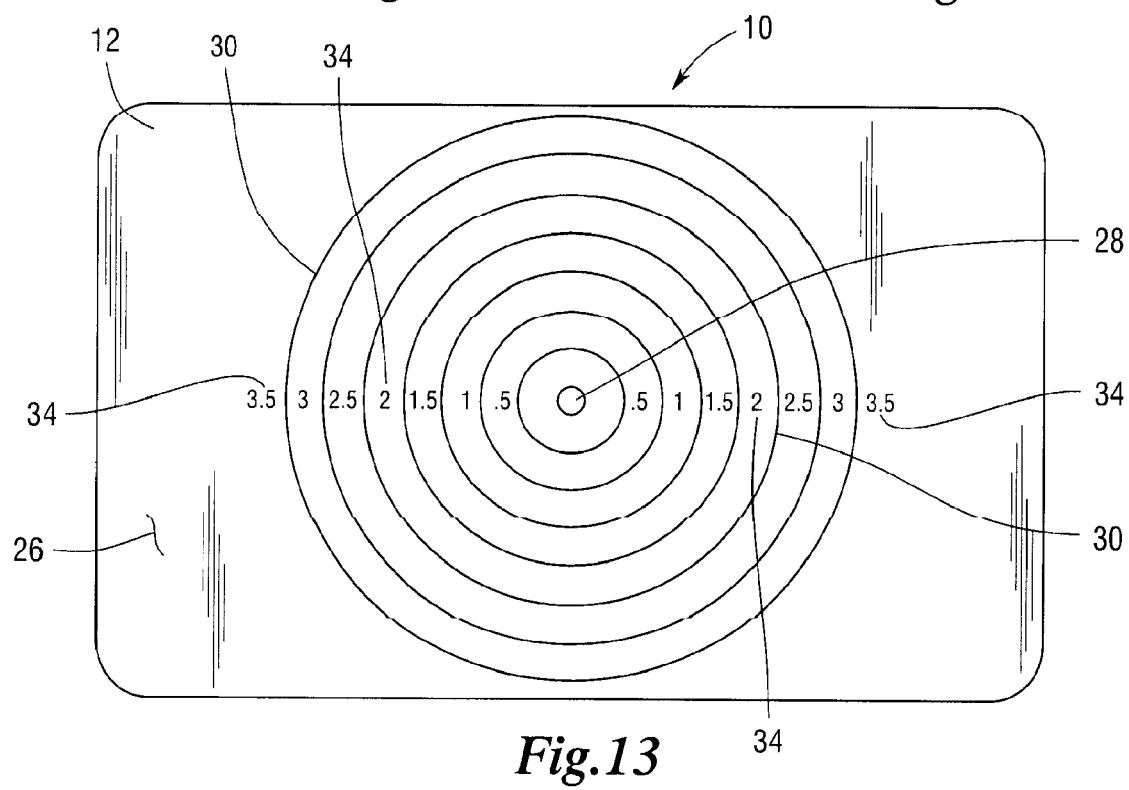
FIG. 13 is a top plan view of the disposable wound measuring device of the present invention illustrating the radial arrangement of the metric scale indicia for each corresponding concentric circle and which are used in measuring the wound along the x and y axes.
Figure 15:
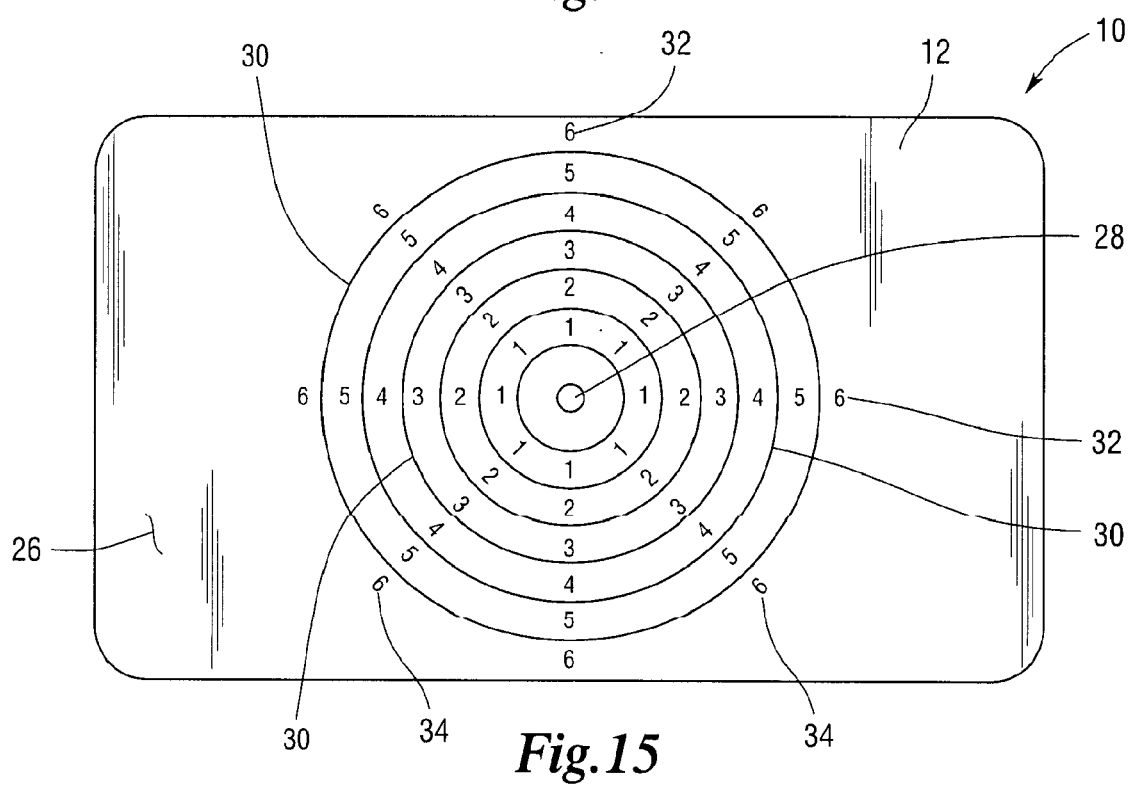
FIG. 15 is a top plan view of the disposable wound measuring device of the present invention illustrating an alternative disposition of numerical indicia adjacent the corresponding concentric circle for the measurement and assessment of larger wounds.

Flexible and conformable clear plastic member 12 includes a lower or under surface 24 that actually contacts tissue 22 and is placed upon and over wound 14 or 16, and an opposite upper surface 26. Extending through clear plastic member 12 is a centrally located aperture 28. Upper surface 26 includes both geometric and numerical wound measurement indicators or indicia printed thereon for quickly, easily and accurately making the simultaneous two-dimensional perimeter 20 wound measurements. The geometrical indicia can include a plurality of concentric wound measurement circles 30 formed on upper surface 26 and concentrically arranged about centrally located aperture 28, and which radially extend toward the peripheral border of clear plastic member 12. As shown on FIGS. 1, 2, 4, 11, 13 and 15, concentric measurement circles 30 fill or cover a substantial portion of upper surface 26 of clear plastic member 12. The spacing of measurement circles 30 from each other can by be any preferred numerical size, increment, or dimension, with such the spacing of such radial numerical increments including ½ of a millimeter, one millimeter, two millimeters, four millimeters or six millimeters, etc. The radial spacing of circles 30 from each other can be dimensioned for accommodating various wound sizes with larger spacing accommodating larger wounds and smaller spacing accommodating smaller wounds. Thus, in FIG. 15, clear plastic card 12 includes a spacing of concentric circles 30 at 1-millimeter increments as denoted by the corresponding numerical indicia 32 to accommodate medium to large-size wounds with the largest circle being at 6 millimeters. In FIG. 11, clear flexible plastic member 12 includes concentric circles 30 arranged thereon at numerical increments of ½ millimeter with the first two circles starting from aperture 28 and thence proceeding at numerical increments of 1 millimeter for the remaining concentric circles 30 out to a distance of 4 millimeters. Thus, clear plastic card 12 of FIG. 11 can be used for smaller-sized wounds while clear plastic card 12 of FIG. 15 can be used for the measurement and assessment of larger wounds. Numerical indicators 34 corresponding to circles 30 of clear plastic member 12 illustrated in FIG. 13 can be for small to mediumsized wounds, and denote a radial spacing of ½ millimeter for circles 30. It should be noted that the numerical measurement scale for concentric circles 30 of clear plastic members 12 is preferably in the metric scale. Numerical indicia 32 and 34 shown on clear plastic cards of FIGS. 11, 13 and 15 provide for a center read indication of overall wound dimensions along the X- and Y-axes, and therefore obviate the need to manipulate—rotate—clear plastic card 12 about margin or perimeter 20 of wound 14 or 16 to attain accurate measurements.

In addition, in order to decrease the need for reorientation of clear plastic card 12 at margin or perimeter 20 of the wound, such as wounds 14 or 16 shown in FIGS. 5, 7 and 8, the numerical measurement indicia can be arranged at or along any radius that is practical depending upon the size (small-size versus large-size wound) of the application. For instance, for a smaller size application the numerical indicators can be arranged adjacent corresponding circles 30 from east to west or from three o'clock to nine o'clock as shown on clear plastic card 12 of FIG. 13 wherein numerical metrical indicia 34 are arranged from left to right or from nine o'clock to three o'clock adjacent corresponding circles 30. The metrical scales or increments of concentric circles 30 of plastic member 12 shown in FIG. 13 are in half-millimeter increments or gradations. For larger-size wounds numerical indicators 34 can be printed at 45 degrees on radius as shown in clear plastic member 12 of FIG. 15.

Figure 1:
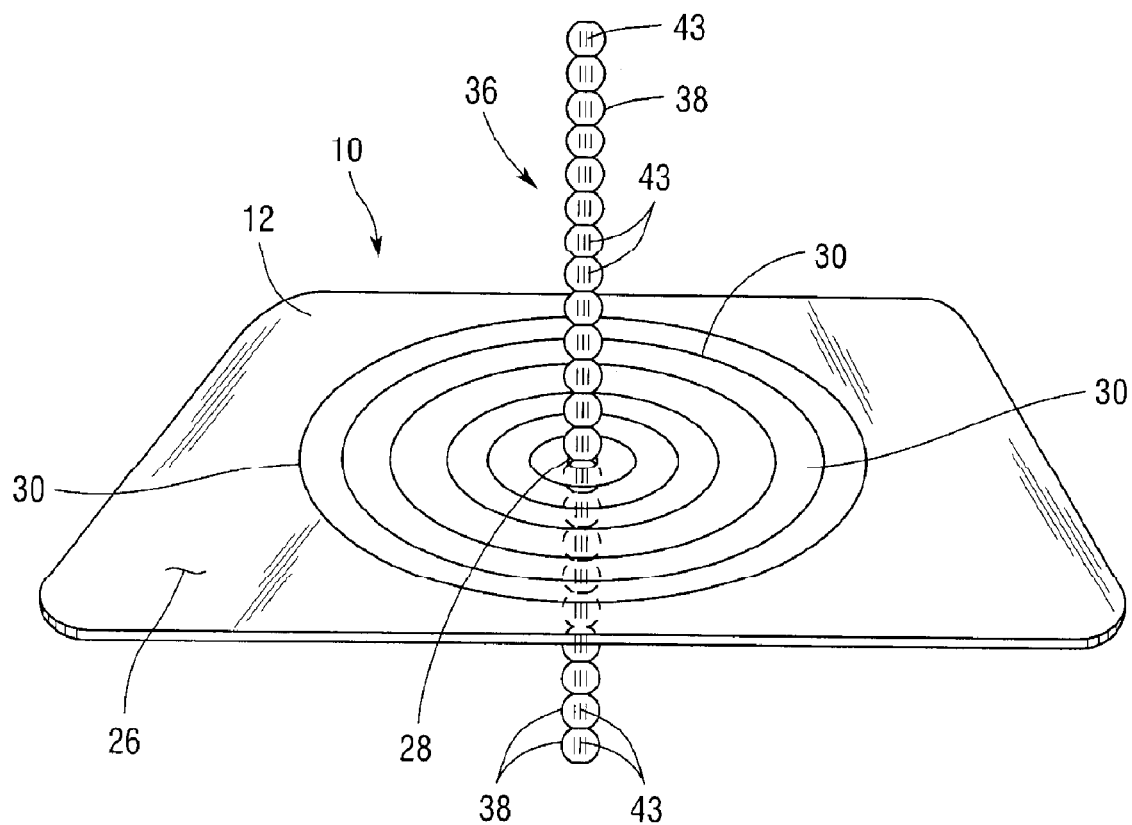
FIG. 1 is a perspective view of the disposable wound measuring device of the present invention illustrating the retention of the beaded depth gauge by the clear plastic member with the beaded depth gauge retained in a perpendicular disposition with respect to the clear plastic member.
Figure 2:
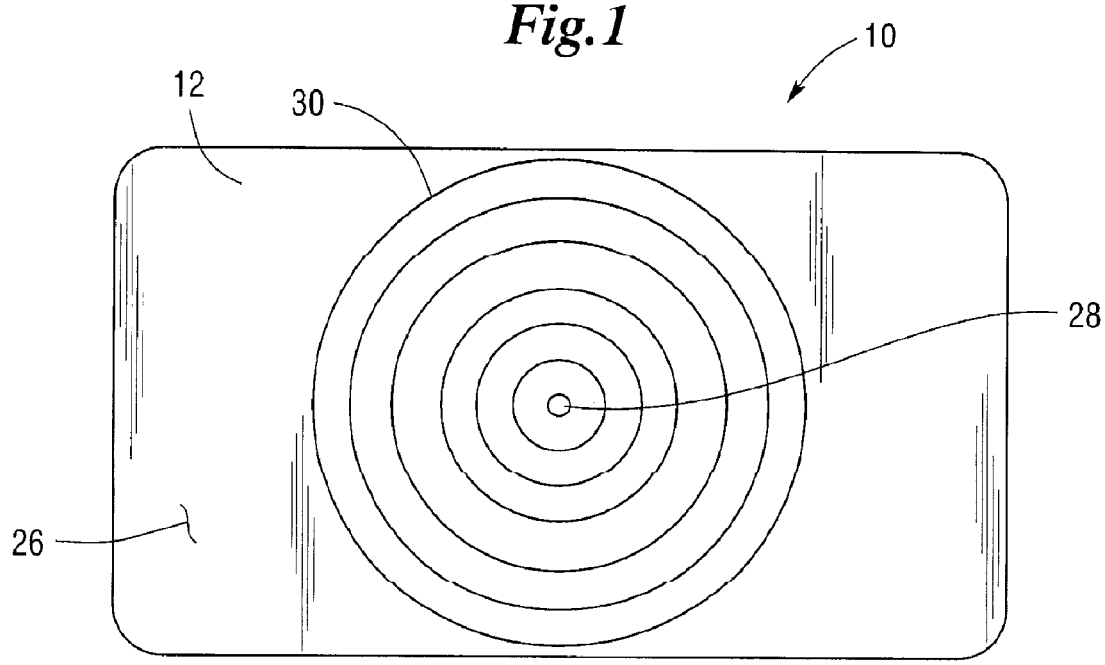
FIG. 2 is a top plan view of the disposable wound measuring device of the present invention illustrating the series of concentric wound measurement circles arranged on the upper surface of the clear plastic member.
Figure 3:
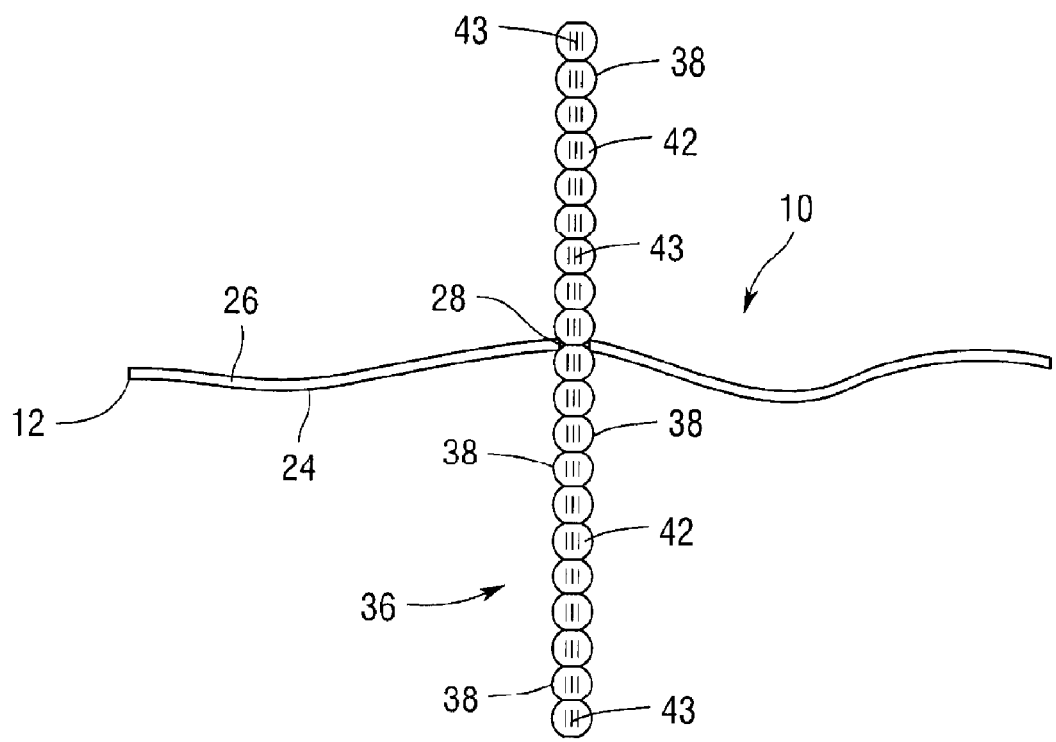
FIG. 3 is a side elevational view of the disposable wound measuring device of the present invention illustrating the engagement of one bead of the depth gauge with the centrally located aperture for self-retention of the depth gauge in position with respect to the clear plastic member.

As shown in FIGS. 1 through 10, and 12, disposable wound measuring device 10 includes an elongated, somewhat pliable beaded depth gauge 36 that is used for measuring the depth of the wound in the Z-axis. Depth gauge 36 is inserted into and through centrally located aperture 28 of clear plastic member 12, and, as indicated in FIGS. 1 and 5, is capable of discrete incremental and reciprocable movement through aperture 28, either toward or away from base 18 of wound 14 or 16, for accurately measuring the depth of wound 14 or 16. In other words, depth gauge 36 is incrementally advanced through centrally located aperture 28 for probing wound 14 or 16, and depth gauge 36 can be incrementally retracted or backed away from wound 14 or 16 in order to precisely find and determine the wound depth or base 18 of wound 14 or 16. During use and operation, depth gauge 36 intersects the horizontal plane of clear plastic member 12 at centrally located aperture 28. In addition, depth gauge 36 includes a series or plurality of axially adjoined beads 38 that facilitate the positive incremental movement and positioning of depth gauge 36 through aperture 28 for wound measurement and the self-retention of depth gauge 36 at any given measurement position relative to clear plastic member 12. Each bead 38 moves or passes through aperture 28 in a discrete, sequential and incremental movement thus allowing for the advancement or retraction of depth gauge 36 for probing wound 14 or 16 for determining and finding the deepest point or base 18. Beads 38 are graduated or axially spaced from each other at various increments, with one preferred increment being one half millimeter 40 from each other as shown in FIG. 5 as taken along the mid-line of each respective bead 38.

As shown in FIG. 6, the diameter of each bead 38 is slightly larger than the diameter of centrally located aperture 28 so that depth gauge 36 can be retained in position by the frictional engagement of external surface 42 of respective bead 38 with centrally located aperture 28. In order to measure the depth of the wound, depth gauge 36 is advanced (and also if need be retracted) one bead 38 at a time, and thus beads 38 allow for the positive incremental sequential advancement of depth gauge 36 into wound 14 or 16 for initially probing wound 14 or 16 in order to find wound base 18 of wound 14 or 16 for measuring the depth of wound 14 or 16. Depth gauge 36 is then self-retained in position after base 18 of wound 14 or 16 is found by the frictional engagement of that respective bead 38 with aperture 28. Wound measuring device 10 is then removed from the site of wound 14 or 16 for ease of reading with depth gauge 36 still retained in that respective position relative to the plane of clear plastic member 12. After the measurements have been charted and recorded, wound measuring device 10 can be disposed. Normally the advancement of depth gauge 36 would be in an axial direction relative to the wound and perpendicular to the horizontal plane of clear plastic member 12. Thus, wound 14 (and the deepest point or base 18 of wound 14) shown in FIGS. 5 and 7 is in general axial alignment with depth gauge 36, and the incremental and sequential movement and positioning of depth gauge 36 would be in the axial direction and in axial alignment with wound 14. Wound measuring device 10 can also be used to measure the depth of an oblique wound, such as the representative oblique wound 16 shown in FIG. 8. For measuring oblique wound 16 of FIG. 8, clear plastic member 12 would be superposed upon wound 16 to establish the horizontal plane of the tissue in the absence of wound 16, and depth gauge 36 would be inclined or tilted and then incrementally advanced for finding the deepest point or base 18 of oblique wound 16. The frictional engagement of the respective bead 38 with centrally located aperture 28 would lock depth gauge 36 in that respective measurement position even though depth gauge 36 is disposed in an inclined, slanted or tilted orientation relative to the plane of clear plastic member 12. Depth gauge 36 will have graduated indicia formed or printed thereon, and, more specifically, each bead 38 will have indicia 43 formed or printed thereon with indicia 43 graduated in preferably ascending metrical dimensions from the lowermost bead 36 to the uppermost bead 36 with indicia 43 on lowermost bead 36 measuring the smallest wound depth and thus proceeding in graduated increments to indicia 43 on uppermost bead 36 measuring the greatest wound depth. Thus, depth gauge 36 and wound measurement circles 30 are used in combination or conjunction to determine and measure the length, width, and depth of wound 14 or 16.

Concentric circles 30 and corresponding numerical indicia 32 and 34 provide for wound measurement in the X- and Y-axis as shown in FIGS. 4, 11, 13 and 15, while beaded depth gauge 36 provides for wound measurement in the Z-axis as also shown in FIGS. 4, 5, 7 and 8. Thus, when device 10 is placed upon representative wounds 14 or 16, as shown in FIGS. 5, 7, and 8, and depth gauge 36 is incrementally advanced for determining the wound depth, wound measurement can be simultaneously taken in all three dimensions or along all three axes—that is along the X-, Y-, and Z-axes 44, 46, and 48, as shown in FIG. 4. Moreover, as shown in FIGS. 5, 7 and 8, clear plastic member 12 conforms to the contour of wound 14 or 16 when superposed thereon, and clear plastic member 12 establishes the effective plane of the tissue that would exist in the absence of the particular wound 14 or 16.

Figure 9:
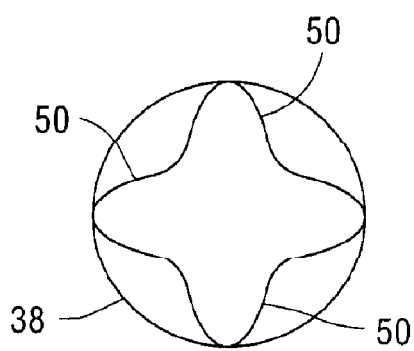
FIG. 9 is a bottom plan view of the disposable wound measuring device of the present invention illustrating cruciate-shaped axial supports for the beads of the depth gauge.
Figure 10:
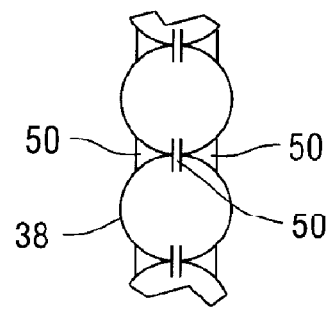
FIG. 10 is a sectioned side elevational view of the disposable wound measuring device of the present invention illustrating the axial supports for the beads of the depth gauge.

As illustrated most particularly in FIGS. 9 and 10, the cross section of beaded depth gauge 36 can be varied in order to produce rigidity, especially for applications where larger wounds are to be measured. For example, axial rigidity-enhancing supports 50 can be added to support each bead 38, and to further attach each bead 38 to adjoining beads 38. Supports 50 have a length that is less than the radius of beads 38 so as not to interfere with the accuracy of measurement or the incremental movement of beads 38 through centrally located aperture 28. Thus, with the inclusion of axial supports 50, the cross section of each bead 38 would be partially cruciate, as shown in FIG. 9.

Figure 12:
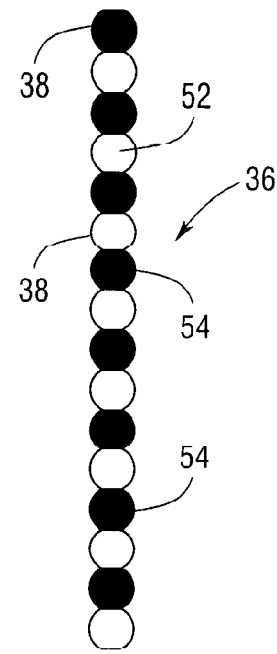
FIG. 12 is a side elevational view of the disposable wound measuring device of the present invention illustrating the depth gauge having alternately colored beads for enhancing depth visibility.
Figure 14:
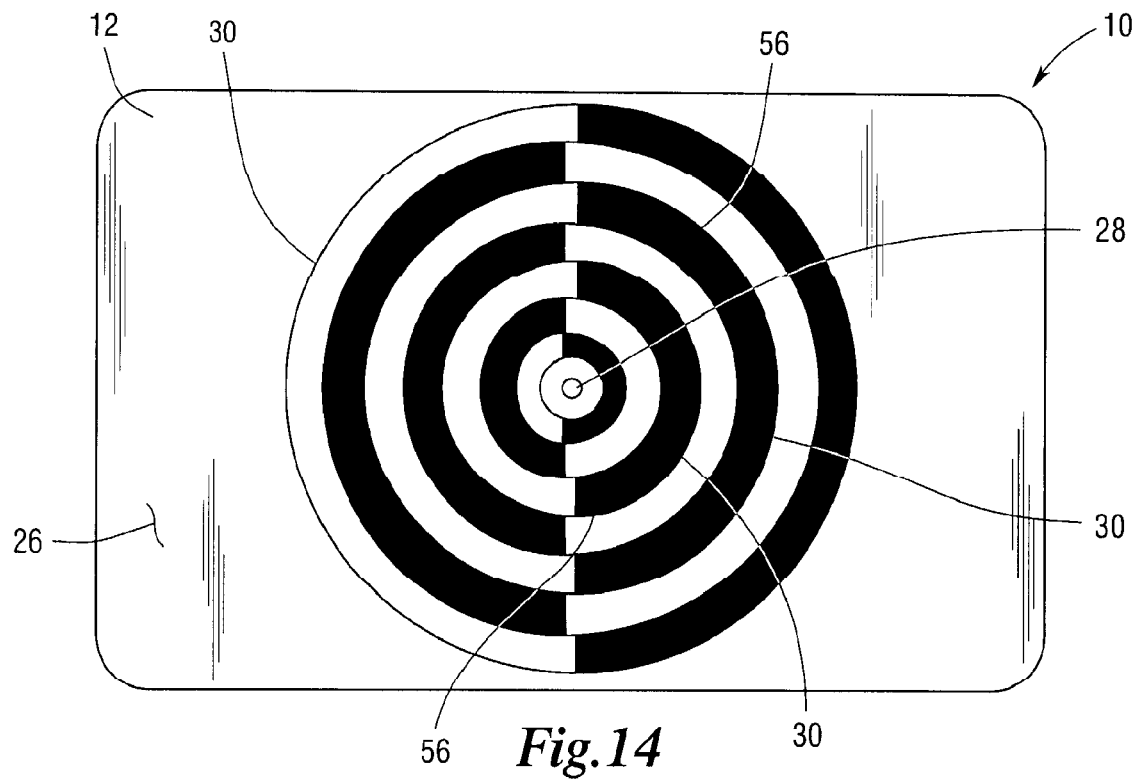
FIG. 14 is a top plan view of the disposable wound measuring device of the present invention illustrating the alternate shading of the concentric circles on the clear plastic member.

In order to enhance readability of beads 38, and to make each bead 38 more readily visually distinguishable from adjoining beads 38, beads 38 can be alternately colored or shaded as shown in FIG. 12. Thus, one bead 38 can be lightly colored or shaded 52 and the adjoining bead 38 can be dark or opaquely colored or shaded 54. Also, as shown in FIG. 14, upper surface 26 wherein each concentric circle 30 is formed can be alternately colored or shaded 56 within circles 30 to enhance the wound measurement process. It should be noted that numerical indicators 32 or 34 that are shown on clear plastic cards of FIGS. 11, 13 and 15 are omitted but could easily be added, as well as other arrangements of numerical indicators.

Figure 16A:
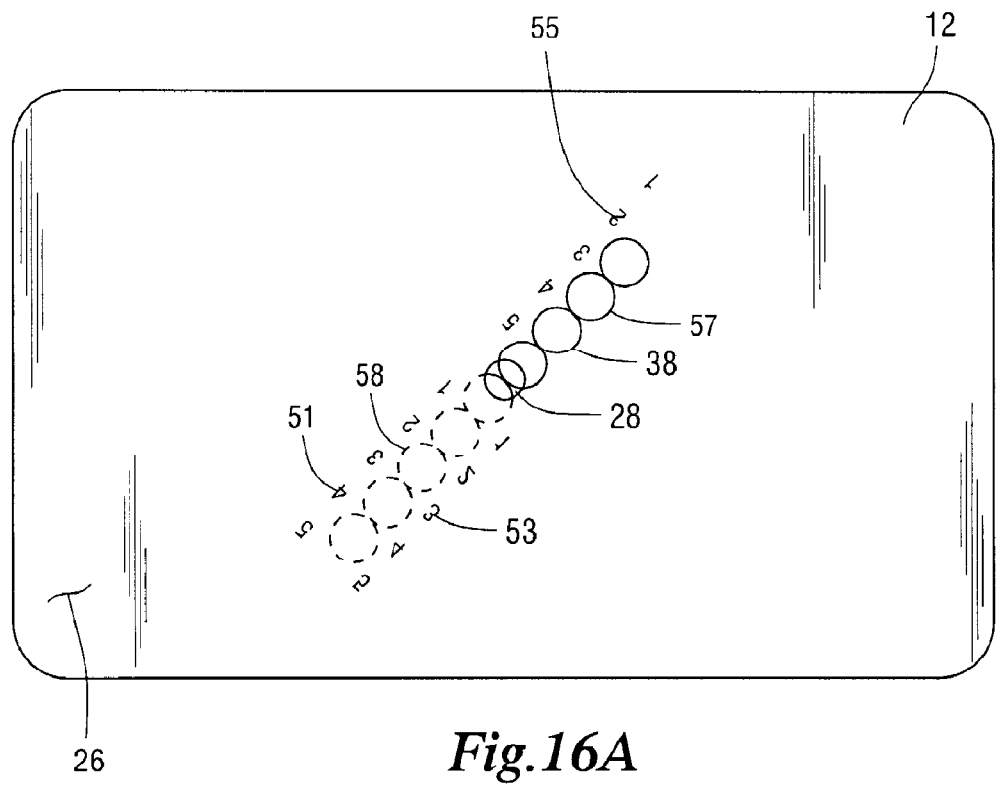
FIG. 16a is a top plan view of the disposable wound measuring device of the present invention illustrating several beads being laid upon the upper surface of the clear plastic card for taking a wound measurement in one millimeter increments from the upper side of the card; and, alternatively illustrating several beads being laid upon the lower surface of the clear plastic card for taking a wound measurement in one millimeter increments from the upper side or from the lower side of the clear plastic card.
Figure 16B:
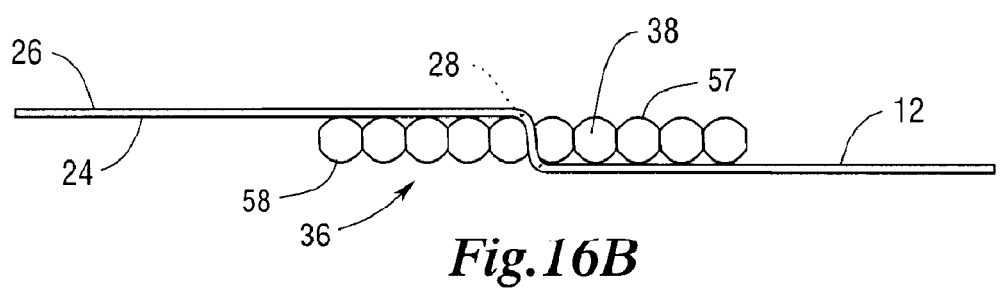
FIG. 16b is a side elevational view of the disposable wound measuring device of the present invention illustrating the flexibility of the clear plastic card in bending about the depth gauge so that an accurate measurement of the wound can be taken.

An additional variation for reading and measuring wound depth is shown in FIGS. 16A and 16B where beads 57 protruding through aperture 28 of clear plastic member 12 can be laid back on upper surface 26 of plastic member 12 and the extent of the wound can then be read on numerically graduated indicia 55 (in descending order from aperture 28 outward). Beads 57 extending above clear plastic member 12 can be manipulated and bent downward for disposition adjacent to upper surface 26 and indicia 55 to obtain an accurate wound measurement. FIG. 16B illustrates the flexibility of clear plastic member 12 in that member 12 can be bent about depth gauge 36 at aperture 28 with depth gauge 36 remaining in its longitudinal extension relative to clear plastic member 12.

Another additional variation for reading wound depth would be demonstrated in FIG. 16B. Once the depth of the wound has been probed and the appropriate beads 38 retained on either side of aperture 28, member 12, and thereby beads 58, are then applied against under surface 24 of transparent card 12 along radially disposed indicia 32 as illustrated in FIG. 15 and the wound depth read directly as visualized from above upper surface 26.

Still another additional variation for reading wound depth would be demonstrated in FIG. 16A. Once the depth of the wound has been probed and the appropriate beads 38 retained on either side of aperture 28, member 12, and thereby beads 58 below card 12, are then applied against the under surface 24 of transparent card 12 along radially disposed indicia 51 on the upper side of member 12 as illustrated in FIG. 16A and the wound depth read directly as visualized from above upper surface 26. In FIG. 16A card 12 indicates the wound depth is two beads, by reading indicia 55 from above card 12.

Further, once the depth of the wound has been probed and the appropriate beads 38 retained on either side of aperture 28, member 12, and thereby beads 58, are then applied against under surface 24 of transparent card 12 along radially disposed indicia 51 and 53 that may be on under surface 24 or upper surface 26 of member 12 as illustrated in FIG. 16A and the wound depth read directly as visualized at beads 58 and reading indicia 51 by looking through upper surface 26 by reading indicia 51. The wound depth can also be read directly as visualized by looking at under surface 24 at beads 58 and reading indicia 53. As drawn in FIG. 16A, both indicia 51 and indicia 53 indicate a wound depth of five beads.

FIG. 17 illustrates an alternative configuration for centrally located aperture 28. Centrally located aperture 28 of FIG. 17 has a cruciate or cross-shape 60 in contrast to the circular shape of aperture 28 as shown, for example, in FIG. 2. In order to accommodate depth gauge 36 for slidable reciprocable incremental movement through aperture 28, aperture 28 may be cross-shaped as shown at 60 in FIG. 17. The configuration and shape of depth gauge 36 must be altered to accommodate different variations of pliable beaded depth gauge 36. Specifically, depth gauge 36 shown in FIGS. 18a and 18b includes a longitudinally extending rib 62 that is coextensive with the extension of depth gauge 36 and joins together beads 38. Rib 62 allows depth gauge 36 to easily slide through the pair of opposed arms of cross-shaped 60 aperture 28 of FIG. 17 for taking the wound measurement.

FIGS. 19 and 20 illustrate other alternative configurations for adjoining beads 38 of depth gauge 36. Thus, in FIG. 19 each bead 38 is adjoined to an adjacent bead 38 by a cylindrical or tubular member 64 for axial alignment of the beads 38. In FIG. 20 each bead 38 is connected to adjacent beads 38 by a fill member 66 that in effect fills in the radial space between adjacent beads 38 and also connects beads 38 in axial alignment to each other. Rib 62 of FIGS. 18a and 18b, tubular member 64 of FIG. 19, and fill member 66 of FIG. 20 can all be formed in any conventional manner as part of and concomitant with the forming or molding of depth gauge 36. Rib 62, tubular member 64 and fill member 66 also maintain the flexibility of depth gauge 36 as shown in FIGS. 16a and 16b.

The foregoing is considered as illustrative only of the principles of the invention, and numerous modifications, alterations and variations will readily occur to those skilled in the art, and thus it is not intended to limit the invention to the exact construction and operation as shown and described, but accordingly to encompass all suitable modifications, alterations, and variations that may fall within the scope of the invention as set forth in the detailed description and the appended claims.

I claim:

1. A disposable wound measuring device for simultaneously measuring the length, width and depth of a wound, comprising:

a clear plastic flexible member for disposition upon the wound;

the clear plastic member having an upper surface and an opposite lower surface that is disposed contiguous to the site of the wound;

the clear plastic member further including an aperture centrally located thereon;

a plurality of wound measurement circles formed on the upper surface and concentrically arranged about the aperture and substantially covering the upper surface of the clear plastic member;

the concentric circles being radially spaced from each other in predetermined increments for allowing the length and width measurements of the wound;

an elongated depth gauge for insertion into and through the centrally located aperture so that the depth gauge is disposed at an orientation perpendicular to the clear plastic member;

the depth gauge further including a plurality of axially adjoined beads with each bead capable of incrementally and sequentially moving through the aperture during the advancement or retraction of the depth gauge for determining a base of the wound and for frictionally engaging the aperture when the base of the wound is found so that the depth gauge can be retained in that respective position relative to the clear plastic member; and, whereupon placement of the clear plastic member upon the wound and the incremental and sequential movement of each bead through the aperture until the base of the wound is found allows for the simultaneous measurement of the length, width and depth of the wound so that the clear plastic member can be lifted from the wound with the depth gauge being self-retained in position by the frictional engagement of one of the plurality of beads with the centrally located aperture so that wound assessment and recordation can be undertaken to be followed by the disposal of the clear plastic member and the depth gauge.

2. The disposable wound measuring device of claim 1 wherein the concentric measurement circles that are radially arranged about the centrally located aperture specifically measure the length and width of the wound.

3. The disposable wound measuring device of claim 2 further comprising a plurality of numerical indicators with each numerical indicator associated with one concentric measurement circle.

4. The disposable wound measuring device of claim 3 wherein each bead is spaced from the adjoining beads by a distance of ½ millimeter as measured from the centerline of each bead to the centerline of the adjoining beads.

5. The disposable wound measuring device of claim 4 wherein the advancement or retraction of the depth gauge through the centrally located aperture is by a positive incremental movement of ½ of a millimeter.

6. The disposable wound measuring device of claim 5 wherein the depth gauge includes a plurality of rigidity enhancing supports for supporting the beads in their axial attachment to each other.

7. The disposable wound measuring device of claim 6 wherein at least some of the beads of the depth gauge can be shaded or colored thereby creating an alternating pattern of colored and non-colored beads to facilitate the measurement of the depth of the wound.

8. A disposable wound measuring device for the simultaneous three-dimensional measurement and assessment of the length, width and depth of a wound, comprising:
a flexible clear plastic card for placement upon the site of the wound;
the flexible clear plastic card having an upper surface and an opposite lower surface that contacts the site of the wound and covers the wound;
the flexible clear plastic card further including an aperture centrally located thereon;
a plurality of wound measurement circles formed on the upper surface that are concentric to the aperture and radially extending outwardly from the aperture;
the concentric circles being radially spaced from each other in predetermined metrical increments thereby facilitating the measurements of the length and width of the wound;
an elongated depth gauge for insertion through the centrally located aperture so that the depth gauge is disposed at an orientation that is perpendicular to the flexible clear plastic card;
the depth gauge further including a plurality of beads adjoined in axial alignment with each other and capable of incremental and sequential passage through the aperture for advancing and retracting the depth gauge so that a deepest point of the wound can be determined; and,
whereupon placement of the flexible plastic card upon the site of the wound and over the wound aligns the depth gauge with the wound so that the incremental and sequential movement of the beads through the aperture can be undertaken for finding the deepest point of the wound simultaneous with the wound measurement circles providing for the measurement of the length and width of the wound whereby the flexible plastic card can then be lifted off the wound with the depth gauge being self-retained in position to the flexible plastic card by the frictional engagement of one of the plurality of beads with the aperture for wound assessment followed by the disposal of the flexible plastic card and the depth gauge.

9. The disposable wound measuring device of claim 8 wherein the wound measurement circles formed on the upper surface of the flexible plastic card overlay the site of the wound for specifically measuring the length and width of the wound.

10. The disposable wound measuring device of claim 9 further comprising a plurality of numerical indicators formed on the upper surface of the flexible plastic card and with each numerical indicator associated with one wound measurement circle to facilitate length and width measurements of the wound.

11. The disposable wound measuring device of claim 10 wherein each bead is spaced from the adjoining beads by a distance of at least ½ millimeter as measured from the centerline of each bead to the centerline of the adjoining beads.

12. The disposable wound measuring device of claim 11 wherein the movement of the depth gauge through the aperture of the flexible plastic card is in sequential positive increments of at least ½ of a millimeter.

13. The disposable wound measuring device of claim 12 wherein the depth gauge includes a plurality of rigidity enhancing supports for supporting the beads in their axial attachment to each other.

14. The disposable wound measuring device of claim 13 wherein at least some of the beads of the depth gauge can be colored for creating an alternating pattern of colored and non-colored beads to thereby visually distinguish the beads from each other and facilitate the measurement of the depth of the wound.

15. A disposable wound measuring device for the simultaneous three-dimensional measurement of the length, width and depth of a wound, comprising:
a flexible clear plastic member having an upper surface, an opposite lower surface for placement on the wound, an aperture centrally located thereon, and a plurality of wound measurement circles formed on the upper surface that are concentric to the aperture and radially extend from the aperture;
a depth gauge including a plurality of beads adjoined to each other in axial alignment thereof with the depth gauge received by the aperture whereby the depth gauge is supported in a vertical orientation with respect to the flexible clear plastic member so that the beads can incrementally and sequentially move through the aperture for advancing and retracting the depth gauge for measuring the depth of the wound; and,
whereupon disposition of the flexible clear plastic member on the site of the wound so that the wound measurement circles overlay the wound in conjunction with the incremental movement of the depth gauge through the aperture for determining the depth of the wound allows for the simultaneous three-dimensional measurement of the length, width and depth of the wound and the flexible clear plastic member can be lifted off the site of the wound with the depth gauge retained in position relative to the flexible clear plastic member by the frictional engagement of one of the plurality of beads with the aperture of the flexible clear plastic member.

16. A disposable wound measuring device for the simultaneous three-dimensional measurement and assessment of the length, width and depth of a wound, comprising:
a flexible clear plastic card for placement upon the site of the wound;
the flexible clear plastic card having an upper surface and an opposite lower surface that is brought into contact with the site of the wound for covering the wound;

the flexible clear plastic card having an aperture centrally located thereon;

the upper surface including numerically graduated indicia radially extending from the aperture for determining the extent of the wound;

an elongated depth gauge for insertion through the centrally located aperture so that the depth gauge can be disposed at an orientation that is perpendicular to the flexible plastic card;

the depth gauge further including a plurality of beads axially aligned and adjoined to each other and capable of incremental and sequential passage through the aperture for advancing and retracting the depth gauge so that a deepest point of the wound can be determined; and whereupon placement of the flexible plastic card over the site of the wound and over the wound for aligning the depth gauge with the wound so that the incremental and sequential movement of the beads through the aperture can be undertaken for finding the deepest point of the wound along a y-axis simultaneous with the numerically graduated indicia providing for the measurement of the wound along an x-axis and a z-axis whereby the flexible plastic card can be lifted up off the wound site with the depth gauge being self-retained in position with respect to the flexible plastic card through the frictional engagement of at least one of the plurality of beads with the aperture so that wound assessment can be obtained followed by the disposal of the flexible plastic card and the depth gauge retained and extending therethrough.

17. The disposable wound measuring device of claim 16 wherein the centrally located aperture has a cross-shaped configuration.

18. The disposable wound measuring device of claim 17 wherein the flexible clear plastic card can be bent about the depth gauge with the depth gauge extending through the clear plastic card and retained therein without disturbing the longitudinal extension of the depth gauge.

19. The disposable wound measuring device of claim 18 further comprising a longitudinal rib for joining the beads in axial alignment to each other with the rib extending the length of the depth gauge.

20. The disposable wound measuring device of claim 19 further comprising a tubular member that joins the beads in axial alignment to each other with the tubular member extending the length of the depth gauge.

* * * * *